(12) United States Patent
Lindsay

(10) Patent No.: US 11,000,445 B2
(45) Date of Patent: May 11, 2021

(54) SUPPORT DEVICE

(71) Applicant: The Diabetic Boot Company Ltd., Aylesbury (GB)

(72) Inventor: Leslie Lindsay, Aylesbury (GB)

(73) Assignee: DBC Medical IOM Limited, Isle of Man (GB)

( * ) Notice: Subject to any disclaimer, the term of this patent is extended or adjusted under 35 U.S.C. 154(b) by 720 days.

(21) Appl. No.: 14/777,217

(22) PCT Filed: Jun. 10, 2015

(86) PCT No.: PCT/GB2015/051699
§ 371 (c)(1),
(2) Date: Sep. 15, 2015

(87) PCT Pub. No.: WO2015/189608
PCT Pub. Date: Dec. 17, 2015

(65) Prior Publication Data
US 2016/0213552 A1 Jul. 28, 2016

(30) Foreign Application Priority Data
Jun. 10, 2014 (GB) ..................................... 1410308

(51) Int. Cl.
*A61H 9/00* (2006.01)
*A61F 5/01* (2006.01)
(Continued)

(52) U.S. Cl.
CPC .............. *A61H 9/0078* (2013.01); *A61B 5/11* (2013.01); *A61B 5/4833* (2013.01);
(Continued)

(58) Field of Classification Search
CPC .......... A61H 9/0078; A61H 2201/5082; A61H 1/0229; A61H 2201/164; A61H 2201/165;
(Continued)

(56) References Cited

U.S. PATENT DOCUMENTS 2,600,957 A   12/1949   Bartis
2,516,872 A *   8/1950   Hauser .................. A61F 5/0127
                                                             602/27
(Continued)

FOREIGN PATENT DOCUMENTS

GB        2488232 A    8/2012
WO    2005051283 A1    6/2005
(Continued)

OTHER PUBLICATIONS

Combined Search and Examination Report, issued in Great Britain Patent Application No. GB1410308.9, dated Jan. 7, 2015 (9 pages).
(Continued)

*Primary Examiner* — Quang D Thanh
(74) *Attorney, Agent, or Firm* — Anderson Gorecki LLP

(57) ABSTRACT

A blood flow stimulating device including a boot including a sole and an upper; a sock disposed within the boot; and a bladder disposed within or on the sock, wherein the bladder is configured to undergo repeated inflation and deflation so as to stimulate blood flow in a wearer of the blood flow stimulating device, wherein the sock further includes a toe region, a heel region and a raised portion between the toe region and the heel region that, in use, reduces the distance between the sock and a foot of a wearer of the blood flow stimulating device at the raised portion of the sock.

12 Claims, 10 Drawing Sheets

(51) Int. Cl.
*A61F 5/34* (2006.01)
*A61B 5/11* (2006.01)
*A61B 5/00* (2006.01)
*A61H 1/02* (2006.01)

(52) U.S. Cl.
CPC ............ *A61B 5/6811* (2013.01); *A61F 5/012* (2013.01); *A61F 5/0111* (2013.01); *A61F 5/0195* (2013.01); *A61F 5/34* (2013.01); *A61B 2562/0257* (2013.01); *A61H 1/0229* (2013.01); *A61H 2201/164* (2013.01); *A61H 2201/165* (2013.01); *A61H 2201/5007* (2013.01); *A61H 2201/5058* (2013.01); *A61H 2201/5071* (2013.01); *A61H 2201/5082* (2013.01); *A61H 2201/5097* (2013.01); *A61H 2205/12* (2013.01); *A61H 2209/00* (2013.01); *A61H 2230/50* (2013.01)

(58) Field of Classification Search
CPC .... A61H 2201/5007; A61H 2201/5071; A61H 2201/5097; A61H 2209/00; A61H 2230/50; A61H 2205/12; A61B 5/11; A61B 5/6811; A61B 5/4833; A61B 2562/0257; A61F 5/0111; A61F 5/012; A61F 5/0195; A61F 5/34
See application file for complete search history.

(56) References Cited

U.S. PATENT DOCUMENTS

| | | | |
|---|---|---|---|
| 3,827,430 A * | 8/1974 | Fadden | A61F 5/0113 602/28 |
| 4,614,180 A | 9/1986 | Gardner et al. | |
| 5,329,705 A | 7/1994 | Grim et al. | |
| 5,367,789 A * | 11/1994 | Lamont | A43B 5/0415 128/892 |
| 5,672,156 A * | 9/1997 | Jimenez Ramos | A43B 7/20 36/89 |
| 5,865,778 A * | 2/1999 | Johnson | A43B 7/20 36/88 |
| 6,090,050 A | 7/2000 | Constantinides | |
| 6,887,213 B2 * | 5/2005 | Smits | A61F 5/0111 602/27 |
| 8,353,968 B2 | 1/2013 | King et al. | |
| 9,642,414 B2 * | 5/2017 | Lindsay | A43B 3/0005 |
| 2004/0003514 A1 | 1/2004 | Cole | |
| 2004/0102727 A1 * | 5/2004 | Smits | A61F 5/0111 602/28 |
| 2004/0111048 A1 | 6/2004 | Jensen et al. | |
| 2004/0158285 A1 * | 8/2004 | Pillai | A61F 5/0102 602/23 |
| 2004/0215111 A1 * | 10/2004 | Bonutti | A61F 5/0102 601/5 |
| 2005/0234378 A1 * | 10/2005 | Ingimundarson | A61F 5/0113 602/23 |
| 2005/0240133 A1 * | 10/2005 | Rooney | A61F 5/0111 602/23 |
| 2007/0179421 A1 | 8/2007 | Farrow | |
| 2007/0260164 A1 * | 11/2007 | Chiodo | A61F 5/0111 602/13 |
| 2008/0269656 A1 | 10/2008 | Arnold et al. | |
| 2009/0019728 A1 | 1/2009 | Roth | |
| 2010/0010606 A1 | 1/2010 | Caffee et al. | |
| 2010/0036306 A1 * | 2/2010 | Lussier | A43B 3/0005 602/65 |
| 2010/0106065 A1 | 4/2010 | Ward | |
| 2010/0324455 A1 | 12/2010 | Rangel et al. | |
| 2011/0040220 A1 | 2/2011 | Holgreen | |
| 2011/0179672 A1 | 7/2011 | Cheng | |
| 2012/0255194 A1 * | 10/2012 | Schwartz | A61F 5/0127 36/19.5 |
| 2013/0018294 A1 * | 1/2013 | Jones | A61F 5/0106 602/27 |
| 2013/0060180 A1 * | 3/2013 | Helm | A61F 5/0127 602/27 |
| 2013/0213144 A1 | 8/2013 | Rice et al. | |
| 2013/0310719 A1 * | 11/2013 | Davis | A61H 9/0085 601/149 |
| 2013/0326912 A1 | 12/2013 | Lindsay et al. | |
| 2014/0034068 A1 * | 2/2014 | Picar | A61F 5/0195 128/888 |
| 2014/0128787 A1 | 5/2014 | Linnane et al. | |

FOREIGN PATENT DOCUMENTS

| | | | |
|---|---|---|---|
| WO | 2011097723 A1 | 8/2011 | |
| WO | WO2012/110763 A1 * | 8/2012 | ............ A43B 13/20 |

OTHER PUBLICATIONS

Combined Search and Examination Report, issued in Great Britain Patent Application No. GB1410308.9, dated Apr. 22, 2015 (5 pages).
Invitation to Pay Additional Search Fees, issued in International Patent Application No. PCT/GB2015/051699, dated Sep. 11, 2015 (5 pages).
International Search Report and Written Opinion, issued in International Patent Application No. PCT/GB2015/051699, dated Nov. 30, 2015 (17 pages).
Pathological Gait Patterns, unknown author and unknown publication date, 2 pages.
Australian Patent Application No. 2015-273282, Office Action dated Sep. 13, 2019, 2 pages.
Chinese Patent Application No. 2015-80030941.2, Translation of Office Action dated Jan. 23, 2019, 20 pages.
Chinese Patent Application No. 2015-80030941.2, Claim and specification amendments submitted in response to Office Action dated Jan. 23, 2019, 30 pages.
Chinese Patent Application No. 2015-80030941.2, Response to Office Action dated Jan. 23, 2019, 14 pages.
Chinese Patent Application No. 2015-80030941.2, Translation of Office Action dated Sep. 9, 2019, 6 pages.
Chinese Patent Application No. 2015-80030941.2, Claim amendments submitted in response to Office Action dated Sep. 9, 2019, 3 pages.
Chinese Patent Application No. 2015-80030941.2, Response to Office Action dated Sep. 9, 2019, 17 pages.
Chinese Patent Application No. 2015-80030941.2, Translation of Office Action dated Jan. 13, 2020, 11 pages.
Chinese Patent Application Serial No. 2015-80030941.2, Claim amendments submitted in response to Office Action dated Jan. 13, 2020, 3 pages.
Chinese Patent Application Serial No. 2015-80030941.2, Response to Office Action dated Jan. 13, 2020, 15 pages.
European Patent Application No. 15729899.3, Communication to European Patent Office dated Aug. 2, 2017, 9 pages.
European Patent Application No. 15729899.3, Communication to European Patent Office dated Jun. 10, 2019, 29 pages.
European Patent Application No. 15729899.3, Notice of Intention to Grant, dated Jul. 1, 2019, 41 pages.
UK Patent Application No. GB1410305.9, Response to Office Action dated Apr. 22, 2015, 12 pages.
UK Patent Application No. GB1410305.9, Office Action dated Apr. 27, 2016, 2 pages.
UK Patent Application No. GB1410305.9, Response to Office Action dated Apr. 27, 2016, 4 pages.
UK Patent Application No. GB1410305.9, Office Action dated Jul. 1, 2016, 1 page.
UK Patent Application No. GB1410305.9, Response to Office Action dated Jul. 1, 2016, 3 pages.
UK Patent Application No. GB1410305.9, Office Action dated Nov. 9, 2016, 1 page.
UK Patent Application No. GB1410305.9, Response to Office Action dated Nov. 9, 2016, 5 pages.

(56) References Cited

OTHER PUBLICATIONS

UK Patent Application No. GB1410305.9, Office Action dated Mar. 31, 2017, 1 page.
UK Patent Application No. GB1410305.9, Response to Office Action dated May 31, 2017, 1 page.
UK Patent Application No. GB1410305.9, Office Action dated Jun. 27, 2017, 3 page.
UK Patent Application No. GB1410305.9, Response to Office Action dated Jun. 27, 2017, 1 page.
UK Patent Application No. GB1410305.9, Certificate of Grant, 1 page.
India Patent Application No. 2016-17041775, Office Action dated Mar. 10, 2020, 6 pages.
Japanese Patent Application No. 2017-517430, Translation of Office Action dated Feb. 25, 2019, 5 pages.
Japanese Patent Application No. 2017-517430, Translation of response to Office Action dated Feb. 25, 2019, 7 pages.
Japanese Patent Application No. 2017-517430, Translation of Office Action dated Dec. 23, 2019, 4 pages.
Japanese Patent Application No. 2017-517430, Translation of response to Office Action dated Dec. 23, 2019, 8 pages.
Saudi Arabia Patent Application No. 2017-517430, Office Action dated Jun. 2020 (with translation), 8 pages.

\* cited by examiner

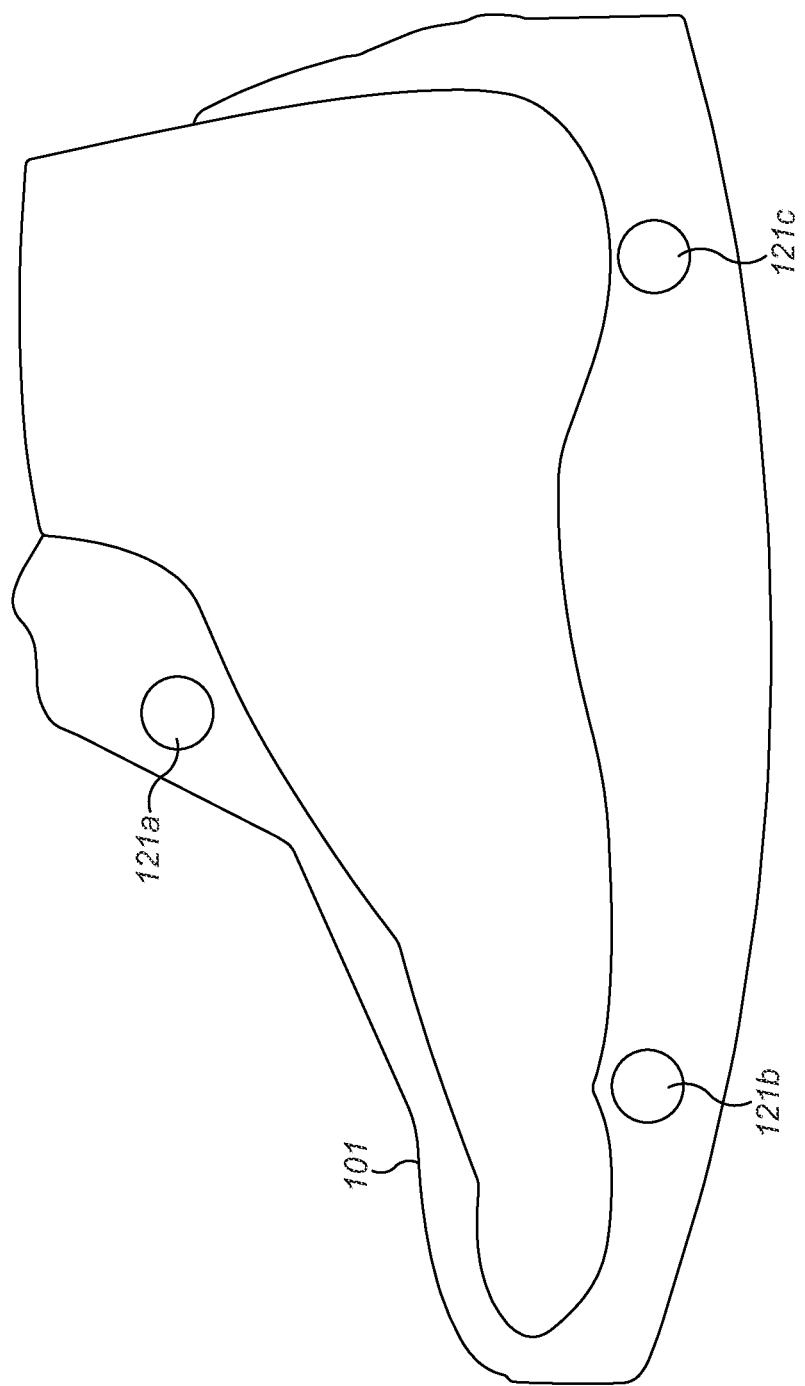

SUPPORT DEVICE

FIELD OF THE INVENTION

The present invention relates generally, but not exclusively, to a support device which enables offloading of a foot of the wearer. The support device may also comprise a blood flow stimulating means which assists in the blood flow of the wearer of the support device.

BACKGROUND OF THE INVENTION

Diabetics often experience poor blood flow, which is described as peripheral ischemia, and may also suffer the loss of feeling in their extremities, known as peripheral sensory neuropathy. If there is loss of feeling in the foot, it is common for injuries to occur without a person suffering from diabetes even noticing, which can result in what is known as diabetic foot ulcer formation. Such wounds can become infected and there is a possibility of the infection spreading to the bone or blood stream which can be life threatening and/or can result in the need for amputation of the limb.

Accordingly, it is desirable to treat such diabetic foot ulcers as quickly as possible so as to reduce the chance of infection and any subsequent spreading of the infection.

To allow the wound to heal, the wound must be kept clean and covered with an advanced wound dressing followed by a technique called offloading, which is well known in the art. Offloading is a technique where, usually, a boot or cast is applied to the foot of a patient so as to immobilise the tri-axis ankle movement of the patient and take pressure off key areas of the sole of the foot.

In normal gait or chain motion, a line of maximum pressure can be mapped through the foot using commercially available test equipment, and typically, this line shows where maximum pressures or "hot spots" will lead to skin breakdown in a diabetic patients. By controlling the line of force/pressure by limiting the rotation of the sub talar joint, offloading redirects/redistributes pressure, and shear and friction forces acting upon a wound that can reduce the chance of an ulcer healing.

During a normal gait cycle, the foot undergoes tri-planar motion which allows lateral heel strike, lateral loading of the fifth metatarsal and then transfer of pressure to the medial side of the foot over the first metatarsal head and push off through the first toe. Such tri-planar motion allows transfer of pressure from the rear foot to the fore foot creating a line of loading from the lateral to the medial side of the foot. A sub talar joint (STJ) is responsible for the majority of tri-plane motion in the foot. If the STJ is restricted, the foot is not able to go through its normal range of the motion and the pattern of loading alters, i.e. a restriction of ankle motion does not allow normal heel strike or toe off, and hip and knee flexion must increase to enable the foot to lift off the ground. Also, with the ankle fixed, the entire surface of the foot will load almost simultaneously as the rear foot and fore foot contact the ground together. This is one potential mechanism of offloading when using Total Contact Casting (TCC).

People who have a normal foot physiology, normal blood supply and tissue oxygenation are not likely to suffer from pressure hot spots that cause tissue damage, unless they wear ill-fitting footwear. Clinicians often refer to "The Gift of Pain", which alerts non sensory neuropathy sufferers to something being "wrong"; footwear being too tight or a stone in your shoe for example. Many diabetic patients have lost this warning signal, and only realise they have a problem when the wound has already occurred.

In considering the diabetic patient as a whole, it is important to realise that they can suffer metabolic changes, leading to abnormal physiology in the foot as the tendons and other structures are affected. These deformities give rise to pressure hot spots while walking and repetitive stress can occur causing the skin breakdown in the form of a diabetic foot ulcer.

The pressures measured during normal walking are an indication of the stress areas of the foot. With the diabetic patient, the foot shape can change, blood supply is often compromised, causing a reduced blood supply (and consequently lowered tissue oxygenation) to the affected area. This can result in an ischemic foot. With loss of feeling in the foot, the pressure area or developing foot ulcer may not be noticed.

As well, a diabetic patient can also experience metabolic changes which can lead to deformities in the foot, e.g. claw toes caused by tendon shortening. These deformities give rise to pressure hot spots and, when walking, repetitive stress can occur causing skin breakdown in the form of a diabetic foot ulcer.

It is very important that offloading be applied to the diabetic foot effectively and safely. TCC has been the optimal therapy for offloading diabetic foot ulcers. However, this technique is not always used because of its many limitations. TCC requires a specialist and takes a long time to apply. The cast must be reapplied at each clinic visit as it must be removed to view the wound. Clinicians are also concerned that the hard cast could damage vulnerable skin. The quality of life issues with TCC include safety and obtrusiveness during sleep or when showering. Casts can cause trips and slipping. Furthermore, TCC casts often raise one leg 4 cm or more above the level of the other leg. This may cause imbalance due to the other leg not requiring a cast. TCC casts should not be used with infected Diabetic foot ulcers as the wound needs to be observed on a regular basis to ensure correct antibiotic therapy is reducing infection. Around 50% of all diabetic foot wounds are infected and, as such, the applicability of TCC casts is greatly limited.

Ankle Foot Orthoses (AFOs) may look similar to offloading devices, but the material they are constructed from is not be sufficiently rigid to allow pressure redistribution/offloading to occur. As such, they are never prescribed for this purpose clinically. Indeed the Medicare reimbursement authorities in the US have expressly forbidden the prescription of AFOs in the treatment of diabetic foot ulcers as they have no functionality.

AFOs are only prescribed for foot drop (the loss of muscle control due to peripheral motor neuropathy or injury such as a stroke, which allows the toes to "dangle" creating a potential trip risk). Whilst many diabetics may suffer from foot drop, the condition bears no relevance to diabetic foot ulcers, other than that the root cause for both conditions is nerve damage. The rigidity of an offloader (e.g. a plaster of paris cast type offloader) is necessary to prevent the tri-planar ankle movements described above. Upon weight bearing, an AFO will flex and allow such a degree of movement as to defeat the controlled pressure redistribution achieved by a true offloading device.

An unrecognised side effect of offloading whilst treating diabetic foot ulcers is a reduced foot and leg pumping action with consequential blood flow back to the heart. The offloading technique described above stops normal foot movements due to the immobilisation effect. These foot movements are important in helping the plantar foot pump, calf muscles and valves return blood flow through the veins back towards the heart against gravity. Accordingly, there is a need to help promote blood flow at the same time as providing the offloading technique described above.

SUMMARY OF INVENTION

There is provided a support device comprising: a support for, in use, engaging a wearer of the support device; a boot comprising a sole and an upper; and an offloader coupled to the support and coupled to the boot, wherein, in use, the support engages the wearer of the support device so as to enable offloading of a foot of the wearer and the offloader is removably coupled to the boot and passes around the outside of the upper.

The support may further comprise a rigid member disposed within the sole and the offloader may be removably coupled to the rigid member.

The offloader of the support device may further comprise a pin (or a plurality of pins) which removably engages the rigid member via a recess in the sole.

The support device may further comprise a blood flow stimulating means.

The blood flow stimulating means may further comprise: a power supply; a fluid pump; a fluid reservoir; a control means; and a bladder.

The power supply, fluid pump, fluid reservoir and control means may each be disposed either on or in the support and the bladder may be disposed within the boot.

The offloader may be disposed entirely outside of the upper.

In use, the support may engage the wearer's leg below the knee.

In use, the offloader may passes from a shin of the wearer to the lateral aspect of the boot.

The offloader may comprise a physiologically designed arc to avoid contact with skin in an ankle area of the wearer.

The rigid member may stiffen the sole so that, in use, the likelihood of pressure points occurring on the foot of the wearer is reduced.

The support device may further comprise a pedometer and a memory configured to store data output by the pedometer. The pedometer readings can be used by the attending clinicians to issue alarms to the patient if they walk more than is beneficial to wound healing.

The support device may further comprise a proximity sensor to detect when the support device is being worn and a memory configured to store data output by the proximity sensor.

The memory may be further configured to store data output by the blood flow stimulating means, and the pedometer. These two readings combined give the attending clinician information, not currently available in any other device, that can assist the clinician advise the patient regarding adherence to prescribed therapy.

There is provided an offloader for use in the support device.

There is provided a support device comprising: a boot comprising a sole and an upper; a sock disposed within the boot; and a bladder disposed within or on the sock, wherein the sock further comprises a toe region, a heel region and a raised portion between the toe region and the heel region that, in use, the reduces the distance between the sock and a foot of a wearer of the support device at the raised portion of the sock.

The bladder may abut against the foot when fully inflated.

The bladder may be disposed within or on the raised portion of sock.

The bladder may abut a plantar plexus of the foot when the bladder is partially inflated or fully inflated.

The bladder may abut a medial plantar arch of the foot when the bladder is partially inflated or fully inflated.

The bladder may have a volume of 40 cm$^3$.

The bladder may have a volume of up to 40 cm$^3$.

There is provided a support device comprising: a proximity sensor; a memory for storing data; a support device for, in use, engaging a wearer of the support device; and an offloader coupled to the support and coupled to the boot, wherein, in use, the support engages the wearer of the support device so as to enable offloading of a foot of the wearer, wherein the proximity sensor detects whether a wearer is wearing the support device and data produced by the proximity sensor is stored on the memory.

The support device may further comprise a pedometer, the pedometer may detect how many steps are taken when the support device is being worn and data produced by the pedometer may be stored on the memory.

There is provided a support device comprising: a proximity sensor; a blood flow stimulating means; a support for, in use, engaging a wearer of the support device; and an offloader coupled to the support and coupled to the boot, wherein, in use, the support engages the wearer of the support device so as to enable offloading of a foot of the wearer, and wherein the proximity sensor detects whether the support device is being worn and the blood flow stimulating means is disabled when the proximity sensor does not detect that the support device is being worn.

The support device may further comprise a boot comprising a sole and an upper;

There is provided a support device comprising: a boot comprising a sole and an upper; and a temperature sensor disposed within the boot in or on the sole and or upper configured to detect skin breakdown and/or a likelihood of skin breakdown on a foot of a wearer of the support device.

The support device may further comprise: a support for, in use, engaging a wearer of the support device; and an offloader coupled to the support and coupled to the boot, wherein, in use, the support engages the wearer of the support device so as to enable offloading of a foot of the wearer.

The offloader may be removably coupled to the boot and may pass around the outside of the upper.

BRIEF DESCRIPTION OF THE DRAWINGS

Embodiments of the present invention will now be described by way of example only with reference to the accompanying drawings, in which:

FIG. 12 depicts an exemplary boot comprising multiple temperature sensors.

DETAILED DESCRIPTION

There is described in what follows a system which enables offloading and which also promotes blood flow.

Several embodiments of an integrated offloading device are described herein and it will be understood that the various features of each of these embodiments, as described in what follows, are not necessarily mutually exclusive from one another and that these features can be combined in any feasible combination, as would be understood by a person skilled in the art.

Throughout the specification, it will be understood that the term "boot" is intended to cover every suitable item of footwear which can be used in the conjunction with each of the devices described herein. Examples of alternative items of footwear include, but are not limited to, boots, shoes, sandals, footwear comprising an upper 104 which extends above the ankle, footwear comprising an upper which stops below the ankle and footwear comprising an open or partially open upper.

Figure 1A:
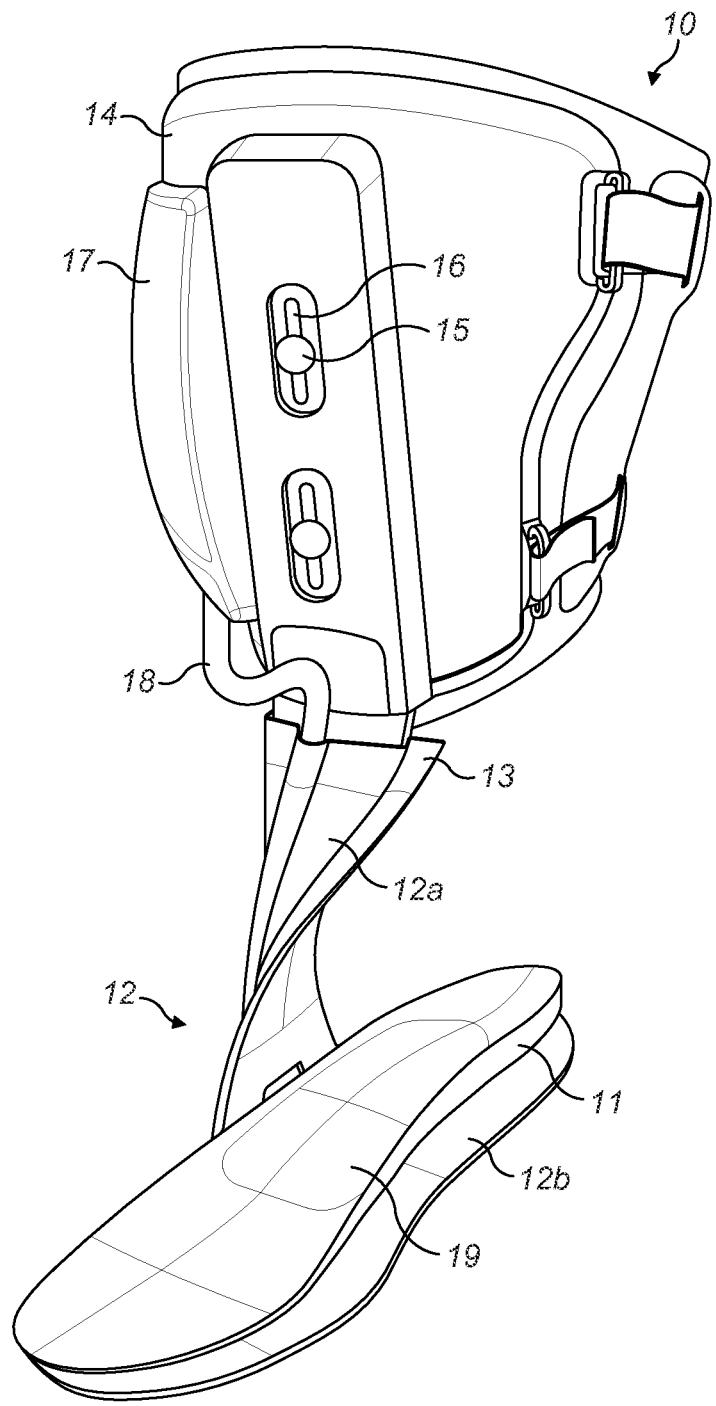
FIG. 1a depicts a comparative example of an integrated offloading device.

FIG. 1a shows a comparative example of an integrated offloading device 10 which provides both the offloading functionality as well as promoting blood flow. The integrated offloading device 10 comprises a shin support structure 14 connected to a sock (otherwise known as an innersole) 11 via an offloading element (or offloader) 12. The offloading element 12 is shown in isolation in FIG. 1b. The sock 11 is disposed on top of a plate portion 12b of the offloading element 12 (shown in FIG. 1b). The lower half of the integrated offloading device 10 is configured to be disposed within a boot (not shown). The lower half of the offloader can be affixed to the boot within the boot, as described in detail below.

The shin support structure 14 comprises means for fixing the offloading element 12 to the shin support structure 14. The embodiment of FIG. 1a shows screws 15 disposed within slide fixing 16 such that the location of the screws can be adjusted within a range of different positions, the screws 15 engaging with the offloading element 12 so as to affix the offloading element to the shin support structure 14.

The shin support structure 14 further comprises a module 17 which contains components which comprise part of a blood flow stimulating means. The module 17 is connected to a conduit 18 which is in turn connected to a bladder 19, disposed within or on the sock 11.

The conduit 18 may be made of a non-expandable material so as to reduce energy loss in the blood flow stimulating means. Throughout this specification, non-expandable is intended to include any material which does not expand under the pressures generated within the blood flow stimulating means described herein.

Figure 1B:
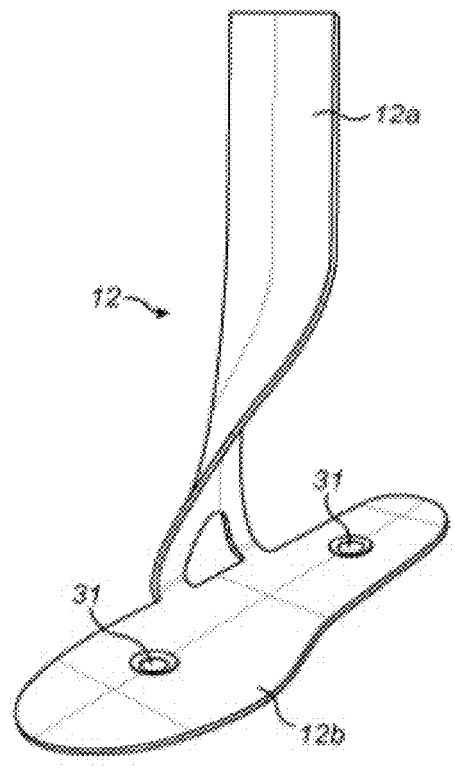
FIG. 1b depicts a comparative example of an offloading element.

The offloading element 12 comprises a stem portion 12a and a plate portion 12b, as shown in FIG. 1b. The stem portion 12a of the offloading element 12 is fixedly attached to the shin support structure 14. As shown in FIGS. 1a and 1b, the stem portion 12a of the offloading element 12 twists from a position in front of the tibia of a wearer of the device, at its end closest to the shin support structure 14, to a position flush with the side of the sole of foot of the wearer of the device. A padded fabric sleeve 13 may be disposed around the outside of the stem 12a of the offloading element 12, as shown in FIG. 1a. The plate portion 12b of the offloading element 12 comprises two holes 31, as shown in FIG. 1b. The plate portion 12b may be securely fastened into the bottom of a boot (not shown) via the holes 31. The sock 11 may then be placed on top of the plate portion 12b of the offloading element 12 (as shown in FIG. 1a). In such an arrangement, the lower half of the stem portion 12a and the entirety of the plate portion 12b of the offloading element 12, as well as the sock 11, are configured to be disposed within a boot (not shown).

The wearer of the integrated offloading device 10 places a boot, to which the plate portion 12b of the offloading element 12 is securely fastened, on their foot and affixes the shin support structure 14 below their knee, such that pressure is transferred from their foot to their shin when standing on the leg on which the integrated offloading device 10 is being worn and preferably such that the knee is still able to flex.

The bladder 19 is disposed within or on the sock 11 and is arranged such that, in use, the bladder 19 abuts the plantar plexus or the a medial plantar arch of a foot of a wearer of the integrated offloading device 10. The module 17 is connected to the bladder 19 via the conduit 18 and which is disposed on or in the shin support structure 14.

Figure 2:
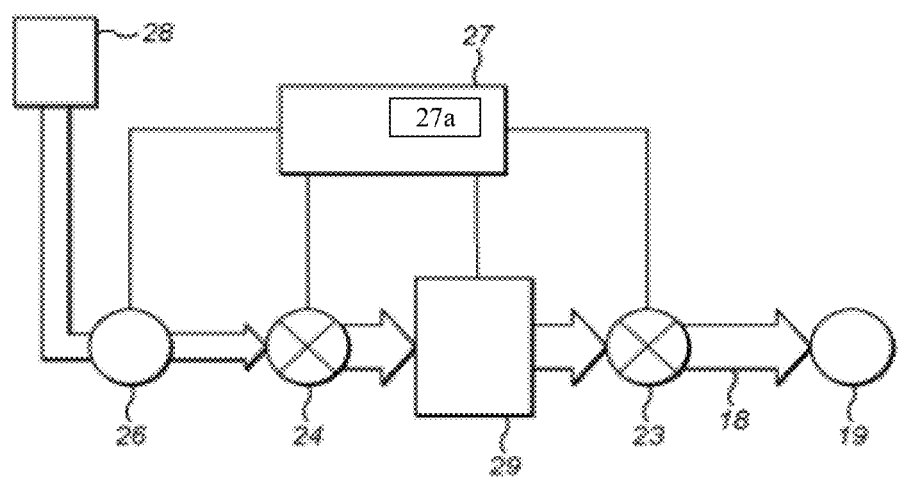
FIG. 2 depicts an exemplary blood flow stimulating system.

The module 17 may further comprise some of the components shown schematically in FIG. 2, namely an electric pump 26 connected to an energy source 28, a controller 27, an atmospheric air inlet (not shown), a fluid reservoir 29, a first valve 24 and a second valve 23.

The components of FIG. 2 collectively form a blood flow stimulating means.

The components of the parts of the blood flow stimulating means disposed within the module may be connected to one another by conduits and these conduits may be made of a non-expandable material so as to reduce energy loss.

It will be understood that the term fluid is intended to include, but is not limited to including, air.

As shown in FIG. 2, the electric pump 26, which is in fluid communication with the atmospheric air inlet (not shown), is in fluid communication with the fluid reservoir 29 via the first valve 24. The fluid reservoir 29 is, in turn, in fluid communication with the bladder 19 via the second valve 23 and the fluid conduit 18. The controller 27 controls the electric pump, the fluid reservoir 29, and the second valve 23. The first valve 24 may also be controlled by the controller 27, but may alternatively be a non-electrical one-way valve. Under control of the controller 27, the electric pump 26 provides air to the reservoir 29 pressurising the reservoir 29 via the first valve 24. The second valve 23 enables short bursts of pressurised air to flow from the reservoir 29 into the bladder 19 via conduit 18. The operation of the second valve 23 is controlled by the controller 27—with reference to memory 27a. A third valve (not shown) may be provided to provide controlled deflation of the bladder 19. The third valve may also be a pressure relief valve configured to prevent over pressurisation of the bladder.

The fluid reservoir 29 is preferably pressurised such that it is able to produce a sharp rise in pressure at the bladder 19 once the second valve 23 is opened meaning that the bladder undergoes rapid inflation. The third valve is preferably configured like a bleed valve such that it can provide for fairly rapid deflation of the bladder 19 (for example over a period of 3 to 4 seconds).

Rapid inflation of the bladder 19 followed by rapid deflation maximises the blood flow promoting effect of the bladder 19. Most commonly, intermittent plantar compression devices squeeze the plantar region over a longer period of time than the rapidly inflating bladder 19 described herein. This rapid action of the bladder 19 delivers a spike rather than a hump of blood flowing back up the veins. This allows the blood to travel further upwards towards the heart.

Preferably, the second valve 23 is open for a sufficiently long period so as to enable the portion of the bladder 19 abutting the plantar plexus/medial plantar arch to urge compression of plantar plexus veins located in the plantar arch region of the foot, such that the subdermal veins at least partially close, thus urging the blood contained therein to return towards the abdomen. It is known that a period of compression of around half a second is sufficient to improve venous drainage, especially if repeated on a regular basis.

Without wishing to be bound by theory, it is thought by the present inventors that repeat compression of the plantar veins releases nitric oxide, a potent vasodilator, which subsequently opens up arterioles bringing more oxygenated blood to the plantar area. It is known that increased oxygenation is beneficial to wound healing and, therefore, it is believed that the integrated offloading devices 10 described herein promote the healing of foot ulcers in this regard.

There are some drawbacks to the above described integrated offloading device 10. The arrangement of the offloading element 12 is such that the boot must fit around the lower portion of the offloading element 12 as described above. Accordingly, the boot would need to be substantially larger than conventional footwear so as to accommodate the lower half of the offloading element 12. Patients who are unaccustomed to wearing larger footwear could find such a boot unwieldy and it could present a tripping hazard.

Furthermore, patients who would use the integrated offloading device 10 often have swollen feet and/or delicate skin. As such, if their skin comes into contact with any part of the stem portion 12a of the offloading element 12, even if the offloading element is padded as described above, unwanted pressure points can arise as the offloading element 12 is made out of a highly rigid material, for example, steel.

The flat plate portion 12b of the offloading element 12 can lead to high heel pressures being experienced by the wearer of the offloading device 10.

Accordingly, there is a need to provide an improved integrated offloading device which overcomes deficiencies in integrated offloading devices such as the device 10 described above.

There is described in what follows a system which enables a much smaller boot to be used in conjunction with an integrated offloading device and which obviates the risk of pressure points arising as a result of the offloading element of an offloading device contacting skin on the foot or ankle of a wearer of the integrated offloading device.

Figure 3:
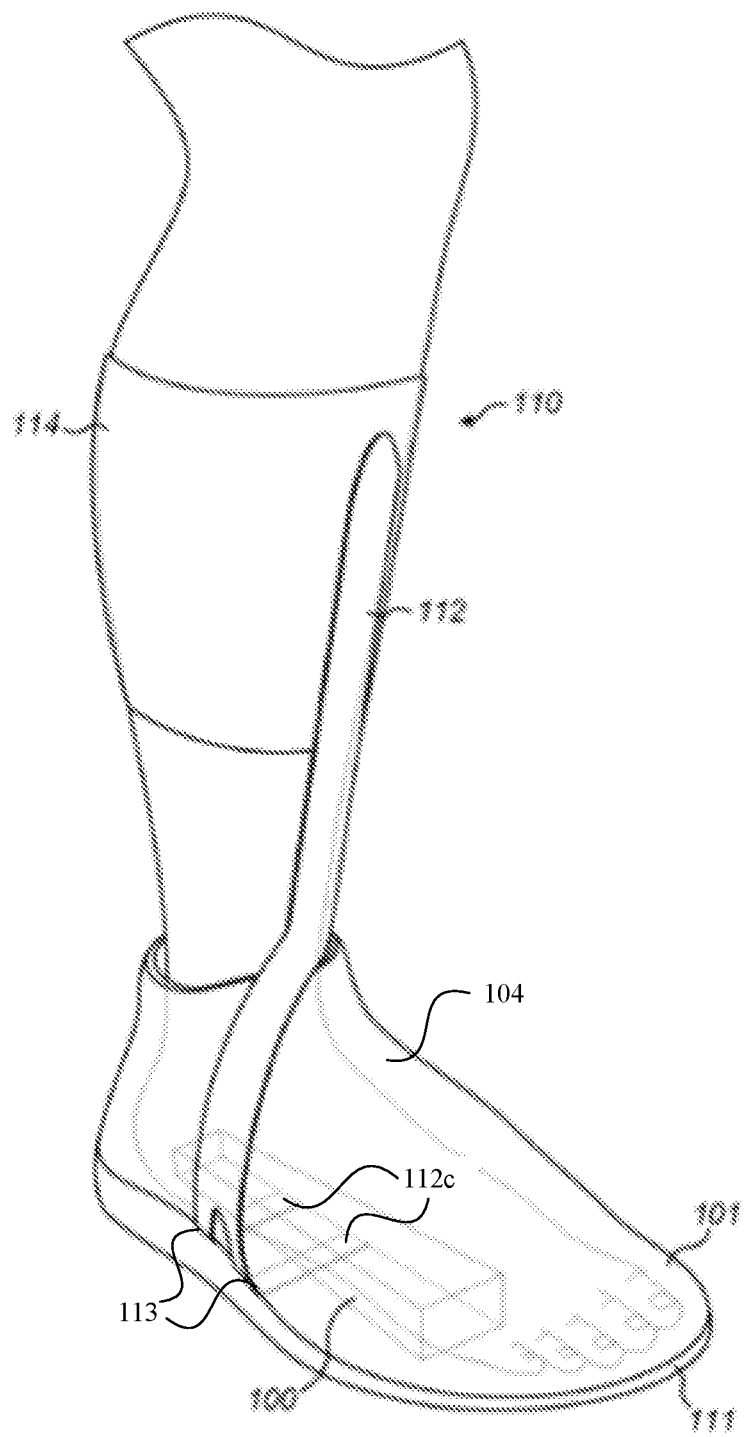
FIG. 3 depicts an exemplary integrated offloading device.

FIG. 3 shows an exemplary integrated offloading device 110. The device comprises a shin support structure 114, a sole 111 and an offloading element (or offloader) 112 disposed between the shin support structure 114 and the sole 111.

Figure 4:
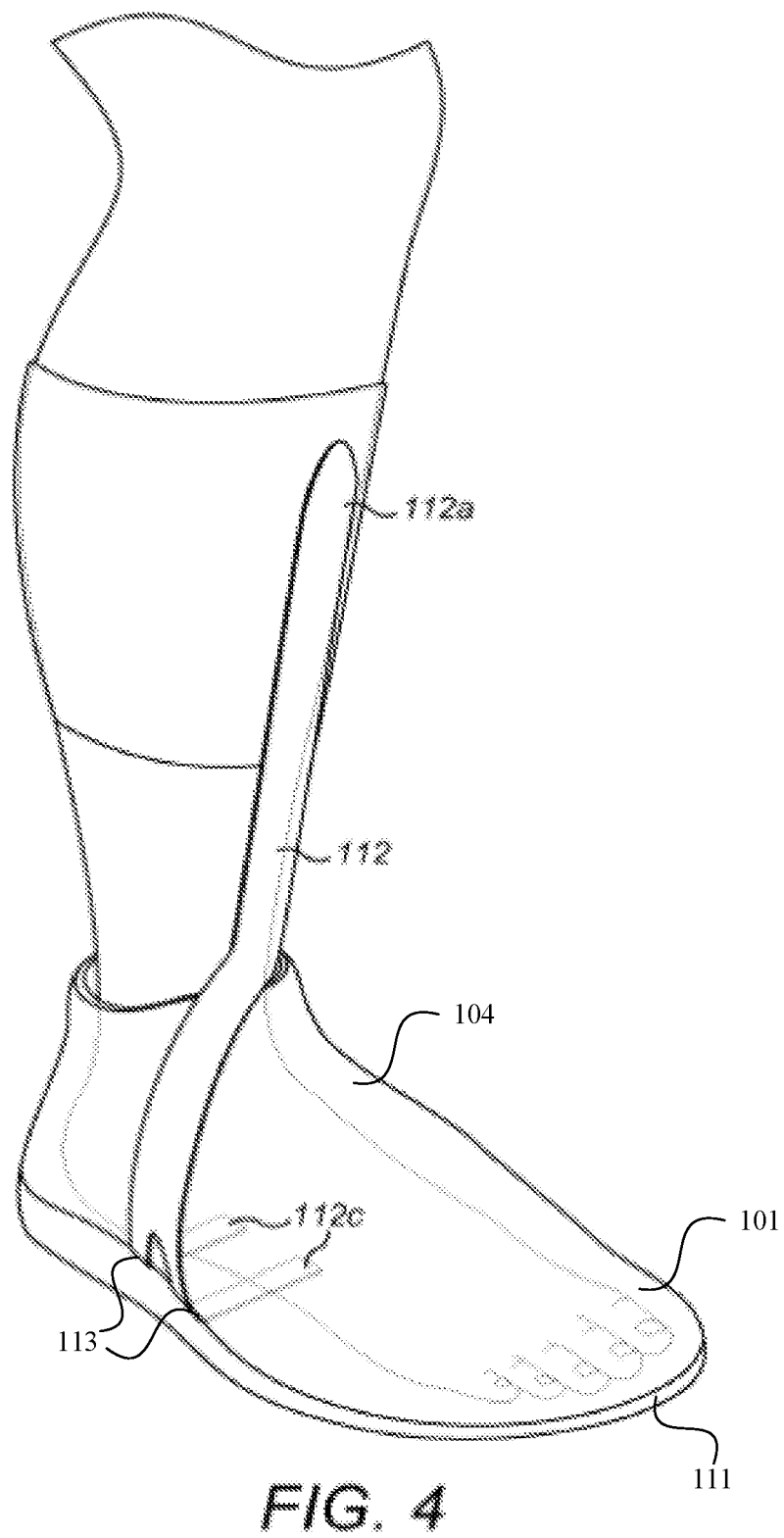
FIG. 4 depicts an exemplary offloading element.

The offloading element 112 comprises a stem portion 112a and a locking portion or pin 112c, which removably engage the rigid member 100 via a recess 113 in the sole 111 of the boot 101, as can be seen in FIG. 3 and FIG. 4.

The top of the stem portion 112a of the offloading element 112 engages with the shin support structure 114 in much the same way as described in relation to the integrated offloading device 10 shown in FIGS. 1a and 1b. The shin support structure 114 is also substantially similar to the shin support structure 14 as has already been described herein and comprises the same module and components.

The offloading element 112 is preferably arranged such that it twists from a position towards the front of the tibia of a wearer of the device, where it intersects with shin support structure 114, preferably to a position flush with the outward facing side of the outside of the boot 101, as shown in FIG. 3.

Although FIG. 3 shows the lower part of the offloading element 112 intersecting with the lateral part of the boot 101, the offloading element 112 may equally intersect with any part of the boot, for example, the heel part or the medial part of the boot. It will also be understood that the offloading element 112 may extend between any suitable point of the shin support structure 114 and any suitable point of the outside of the boot 101 so as to provide for the offloading functionality, as would be understood by the skilled person.

The boot 101 may be specially designed so as to minimise any internal abrasive forces when the boot 101 is being worn. For example, the boot 101 may have no exposed internal stitching or seams capable of rubbing away frail diabetic skin.

The boot 101 comprises a rigid member 100 disposed within the sole of the boot, as shown in FIG. 3. The rigid member comprises at least one female mating portion (the rigid member shown in FIG. 3 comprises two female mating portions) which engages with the locking portion or pin 112c of the offloading element 112.

As shown in FIG. 3, the twist in the offloading element 112 is such that the locking portion or pin 112c is located at a lateral part of the boot 101. The locking portion or pin 112c comprises at least one male portion, each male portion entering through an orifice/recess 113 in the sole 111 of boot 101 and engaging with the female portion of the rigid member 100 disposed within the sole 111 of the boot 101.

The nature of this engagement is such that sufficient rigidity is provided to enable offloading of the foot, locking tri-axial ankle movement as described previously, of the wearer via the engagements between the rigid member 100, the offloading element 112 and the shin support structure 114. By locking the ankle, pressure hot spots are prevented. Further, the speed of the "foot slap", which creates peak pressures in the metatarsal area and toe extremities, is controlled. Limiting the movement of the ankle causes the less flexible knee and hip joints to articulate to allow chain motion, but at a slower pace.

The design of the offloading device 110 addresses another concern that troubles diabetic foot ulcer patients. Peripheral sensory neuropathy often prevents diabetic foot ulcer patients feeling if their feet are correctly located in the footwear component. The offloading device 110 design allows the boot 101 to be fitted correctly first, with visual sighting by the patient, then the shin support structure 114 and the offloading element (or offloader) 112 can be fitted subsequently. Current designs of offloader interfere with clear sight of the foot placement within the device.

Advantageously, the offloading element 112 is not disposed within the boot 101 and the aforementioned issues arising in relation to the substantially rigid offloading element 12 being disposed against the skin of the wearer of the integrated offloading device 10, specifically the skin around the foot and ankle, do not arise.

A sock 11 is provided within the boot 101 of the exemplary integrated offloading device 110. As described in relation to the integrated offloading device 10, the sock has a bladder disposed within or on it and the bladder is connected to the remainder of the blood flow stimulating means via conduit 18 (as shown in FIG. 2), the remainder of blood flow stimulating means being located within the shin support structure 114. As such, the exemplary offloading device 110 also provides for blood flow stimulation in conjunction with offloading.

Advantageously, the rigid member 100 stiffens the sole of the boot 101 so that, in use, only very limited flex in the boot sole occurs, reducing the likelihood of pressure points occurring on the foot of the wearer of the integrated offloading device 110 as the line of force/pressure during a gait cycle is controlled and spread out compared to the line of maximum pressure during a normal gait cycle where an offloader is not being used, which means that the maximum pressures or "hot spots", which can lead to skin breakdown in a diabetic patients, are avoided.

After a course of treatment is completed, the shin support structure 14 and the offloading element 112 may be removed. The boot 101 will continue to provide enhanced offloading capability over regular footwear due to the increased rigidity of its sole. As such, pressure, and shear and friction forces are reduced and the likelihood of the occurrence or reoccurrence of ulcers is reduced.

Another advantage is that the boot 101 can be used on its own (i.e. removing the offloading element 12 and shin support structure 14 after a period treatment), for example for treatment of acute conditions, meaning that the patient can be discouraged from going back to wearing ill-fitting shoes and/or shoes with exposed internal stitching, capable of rubbing away frail diabetic skin when offloading is no longer required or possible.

It is a concern to skilled practitioners that providing a pair of diabetic boots that reduce the social stigma due to their normal appearance will encourage patients to walk more. The clinical recommendation to a diabetic foot ulcer patient wearing the current invention will be to wear it allowing blood pumping for several hours per day, but not to walk unless absolutely necessary, so as to promote healing of the foot ulcer. The clinician needs to be able to check that the patient is abiding by this advice.

The integrated offloading device 110 may further comprise a pedometer and a memory configured to store the data output of the pedometer.

The inclusion of a pedometer would enable a clinician to ascertain how many steps the patient has taken during a treatment period.

The integrated offloading device 110 may also comprise a proximity sensor to detect whether the device is being worn or not and/or how many hours pumping has taken place. This data may be stored on the memory and downloaded at clinic or transmitted remotely to a clinician.

Advantageously, the inclusion of a proximity sensor would enable a clinician to ascertain how often the boot is worn during a treatment period. This can be combined with data from the pedometer to ascertain how many steps a patient has taken whilst wearing the integrated offloading device 110.

The integrated offloading device 110 may be configured such that the blood flow stimulating means will not operate if the proximity sensor detects that the device 110 is not being worn.

Data from the controller 27 may also be stored on the memory such that the clinician is able to ascertain how often the bladder has inflated during a treatment period. Advantageously, this provides the clinician with means for measuring the compliance of a particular patient with regards to the treatment.

The integrated offloading device 110 may be used with a boot designed with a rocker sole to allow better pressure distribution during normal gait.

Rocker bottoms, front and back, are well known to those skilled in the art.

A rocker sole has a toe section that is raised upwards, creating a gap between the ground and the sole of the footwear. For a diabetic with tri-axial ankle motion locked in an offloading boot, a rocker sole allows a small transfer of weight forward to create the start of the gait cycle, and reduce peak interface pressures at the toes. A rocker heel may also be provided to reduce downward pressure upon heel strike, transitioning into forward movement smoothly, thus preventing the foot from slapping down.

The integrated offloading device 110 may be used with a boot which further comprises straps designed to be easily secured by patients with poor eyesight and limited grip strength. The straps may be double return Velcro™ (hook and loop fastener) straps with a mid-point which gives users a guide as neuropaths can't feel tightness as a normal person would. The correct securing of the boot is important as the bladder 19 will seek to lift the foot upwards unless constrained by the boot.

Neuropathic patients represent around 60% of patients with foot ulceration. They have no sensation in their feet, so often over tighten footwear fastenings to the point where skin abrasion or even local ischemia occurs. The boot 101 may have marked straps to give an indication as to how tight they should be in the absence of patient sensory feedback.

Figure 5:
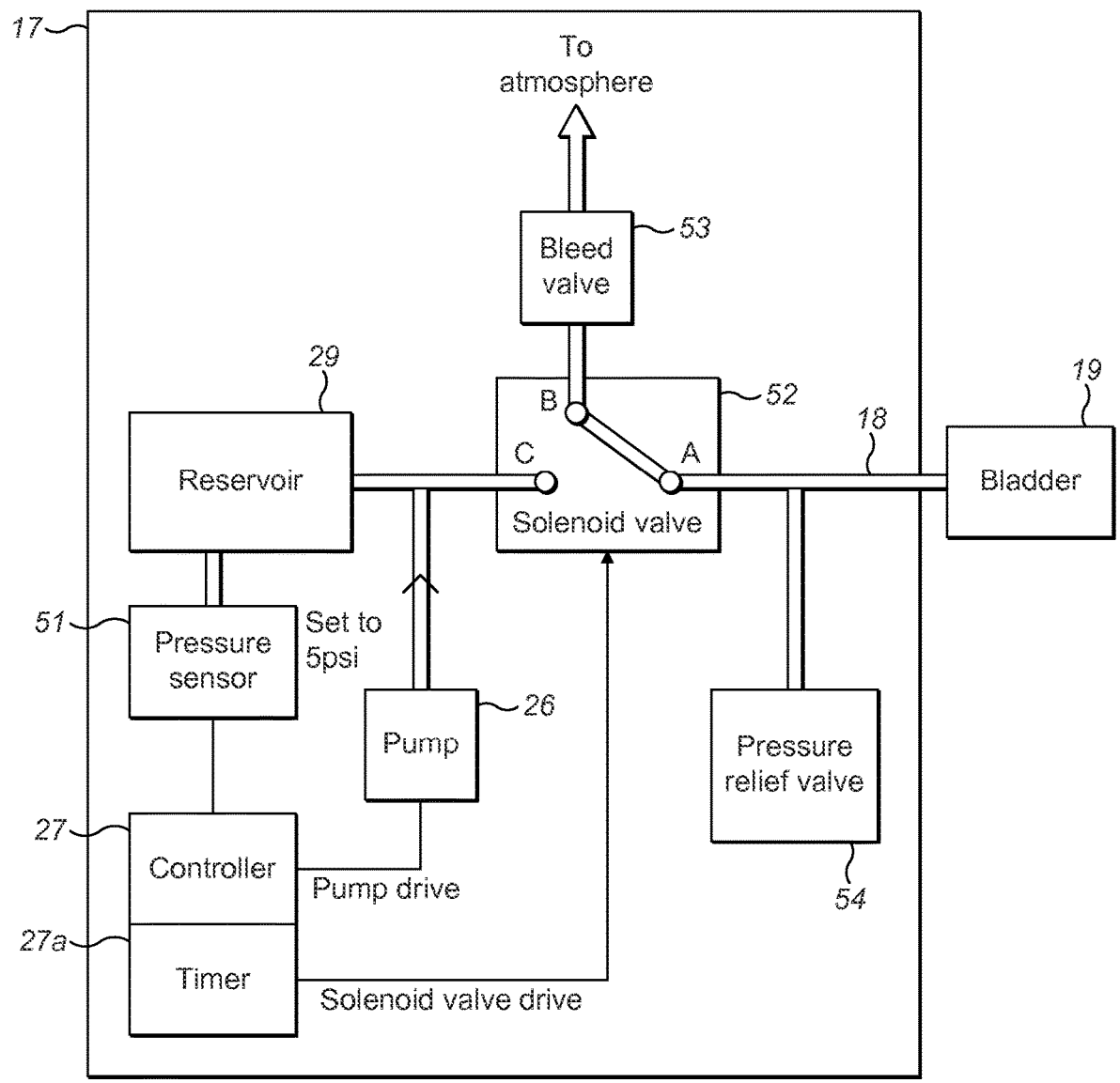
FIG. 5 depicts a schematic diagram of an alternative blood flow stimulating means.

FIG. 5 is a schematic diagram of an alternative blood flow stimulating means. Many of the components are the same as or similar to those of the blood flow stimulating means shown in FIG. 2 and the same reference numerals have been used for these components.

The blood flow stimulating means comprising a module 17 comprising a pump 26, a controller 27, a timer in communication with the controller 27a, a reservoir 29, a pressure sensor 51, a solenoid valve 52, a bleed valve 53, and a pressure relief valve 54 which acts to keep the pressure below a predetermined upper threshold (for example, 23.4 kPa (3.4 psi)). Also shown is the conduit 18 which connects the solenoid valve 52 to the bladder 19. The controller 27 is in communication with the pump 26, the solenoid valve 52 and the pressure sensor 51. The pump 26 is in fluid communication with the reservoir 29 and the solenoid valve 52. A pressure sensor 51 is in communication with the reservoir 29 such that when the pressure in the reservoir 29 reaches a predetermined value (for example, 94.5 kPa (5 psi)) the controller 27 switches the pump 26 off such that no more fluid is pumped into the reservoir.

The solenoid valve 52 is connected to the bladder 19, the reservoir 29 and the bleed valve 53. As shown in FIG. 5, the solenoid valve 52 is able to switch between a configuration A-B where the bladder 19 is in fluid communication with the bleed valve 53 and a configuration A-C where the bladder 19 is in fluid communication with the reservoir 29 via the solenoid valve 52.

Figure 6:
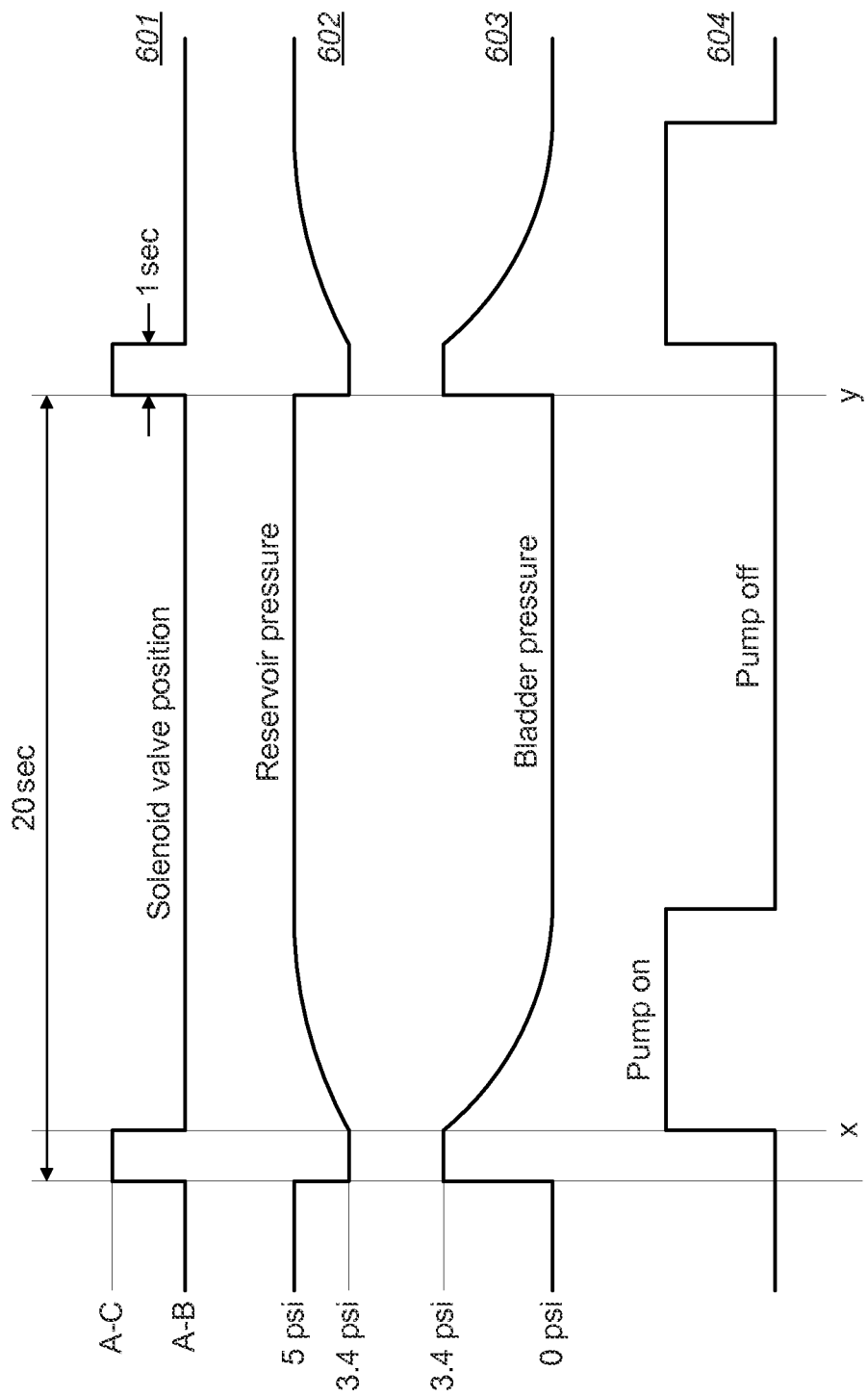
FIG. 6 depicts exemplary timings and pressure values for a full cycle of operation of the blood flow stimulating means shown in FIG. 5.

FIG. 6 shows exemplary timings and pressure values for a full cycle in the operation of the blood flow stimulating means shown in FIG. 5. 601 shows the position of the solenoid valve 52, 602 shows the pressure of the fluid in the reservoir 29 during a cycle between exemplary lower and upper values 23.4 kPa (3.4 psi) and 94.5 kPa (5 psi), 603 shows the pressure of the fluid in the bladder during a cycle between exemplary lower and upper values 0 kPa (0 psi) and 23.4 kPa (3.4 psi) and 604 shows whether the pump 26 is switched on or off.

The cycle shown in FIG. 6 starts with the solenoid valve 52 in the A-C position. The previously pressurized reservoir 29 is thus in fluid communication with both the bladder 19 and the pressure valve 54. The pressure of the bladder and reservoir is maintained at the exemplary value of 23.4 kPa (3.4 psi) by the pressure relief valve 54.

Although an exemplary pressure of 23.4 kPa (3.4 psi) has been described, any suitable pressure, i.e. sufficient to produce the blood flow stimulating effect, may be used, as would be understood by a person skilled in the art.

At time X (1 second after the start time) the controller switches the solenoid valve 52 to the A-B configuration where the bladder 19 is in communication with the bleed valve 53. The pressure inside the bladder 19 then drops to 0 kPa (0 psi) as the fluid inside of the bladder is released into the atmosphere via the bleed valve 53. Once the solenoid valve 52 has been switched to the A-B position, the controller 27 switches on the pump 26 and the reservoir 29 is pressurized to 94.5 kPa (5 psi). Once the reservoir reaches an exemplary predetermined pressure of 94.5 kPa (5 psi), the pressure sensor 51 communicates with the controller 27 signaling that the predetermined pressure has been reached and the controller 27 switches off the pump 26. After a predetermined period of 19 seconds since time X has elapsed, the solenoid valve 52 is once more switched to the A-C position at time Y such that the bladder 19 is put into fluid communication with the pressurised reservoir 29 and is inflated and the cycle repeats with the solenoid valve 52 being once more switched to the A-B after a predetermined period of time (for example, 1 second) after time Y has elapsed.

The structure of the offloading element 112 is used to provide structural support to the conduit 18, which brings pressure from the reservoir 29 to the bladder 19. The conduit may pass through a channel in the outside of the sole 111 of the boot 101 to reach the bladder 19.

Figure 7:
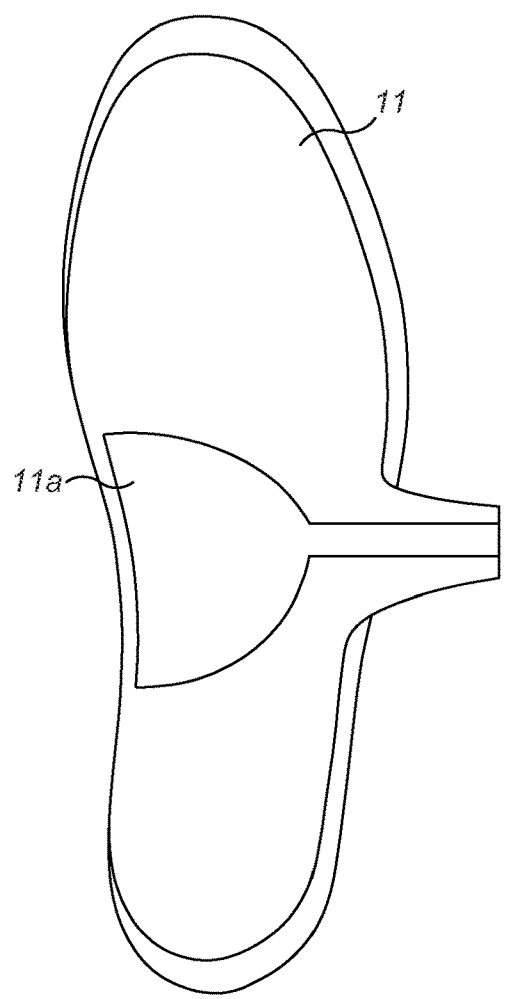
FIG. 7 depicts the underside of an exemplary sock.

FIG. 7 shows the underside of an exemplary sock 11. FIG. 7 shows a recess 110 in the underside of the sock 11 for housing the bladder 19 and the conduit 18.

Figure 8:
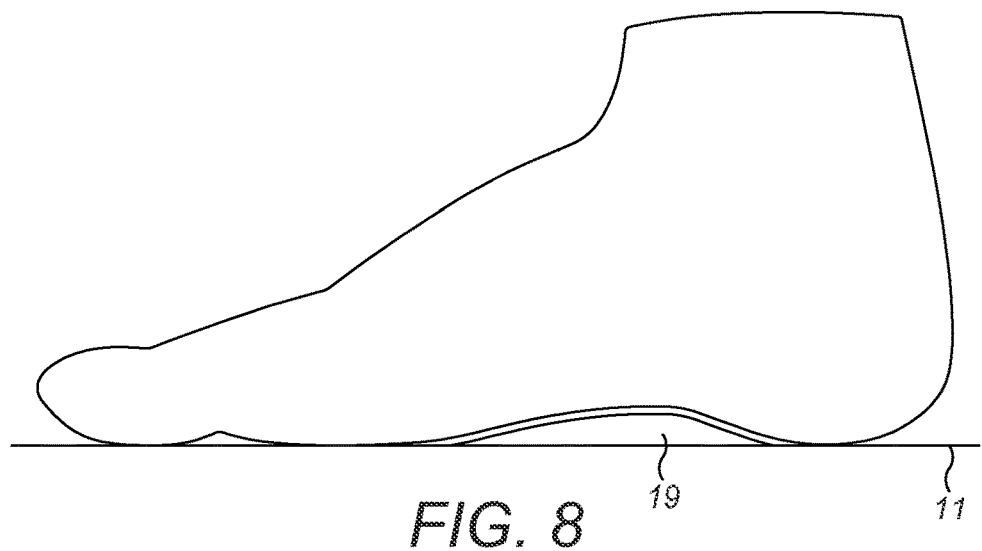
FIG. 8 depicts a side-on view of an exemplary sock.

FIG. 8 shows a side-on view of an exemplary sock 11 with the bladder 19 inflated. The Figure also shows a foot in the position that it would be in when a user of the integrated offloading device 10 is wearing said device. It is apparent from FIG. 8 that the inflated bladder 19 is abutting the plantar plexus/medial plantar arch of the foot.

Figure 9A:
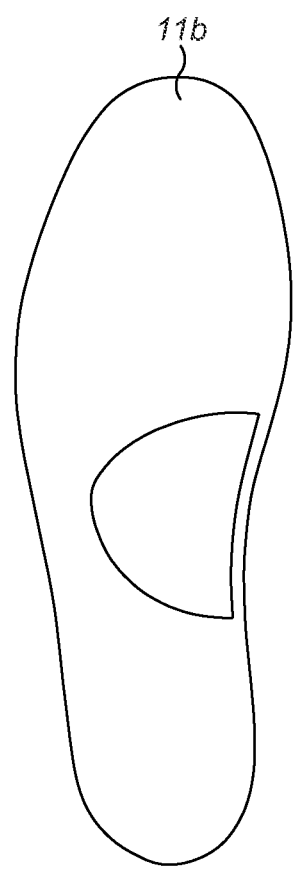
FIGS. 9a to 9c depict another exemplary sock.
Figure 9B:
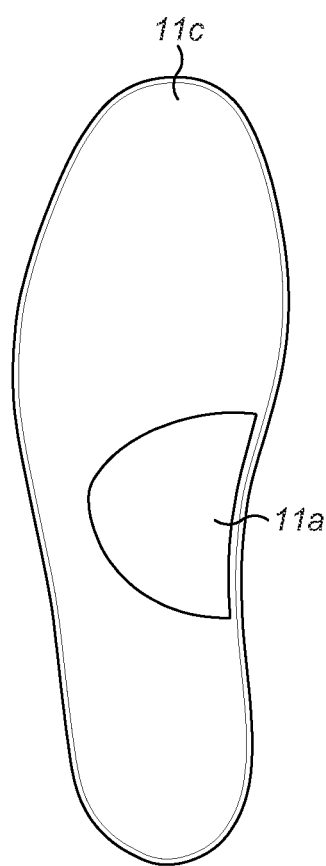
Figure 9C:
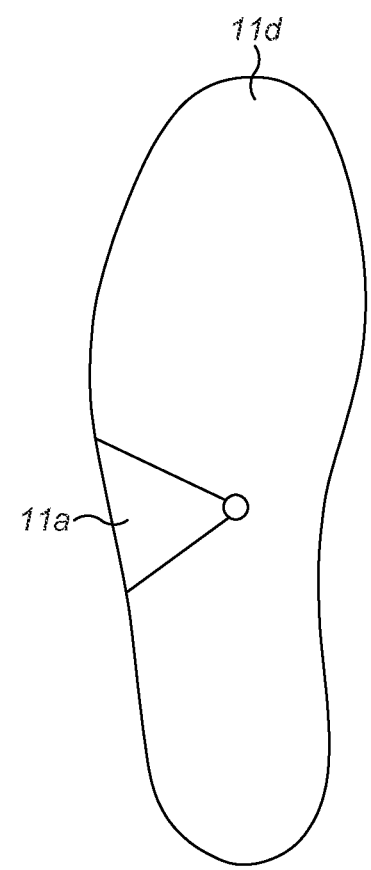

FIGS. 9a to 9c show another exemplary sock wherein the sock is comprised of a top 11b, a middle 11c and a bottom 11d. FIGS. 9b and 9c show the recess 11a for housing the bladder 19 and the conduit 18.

Figure 10:
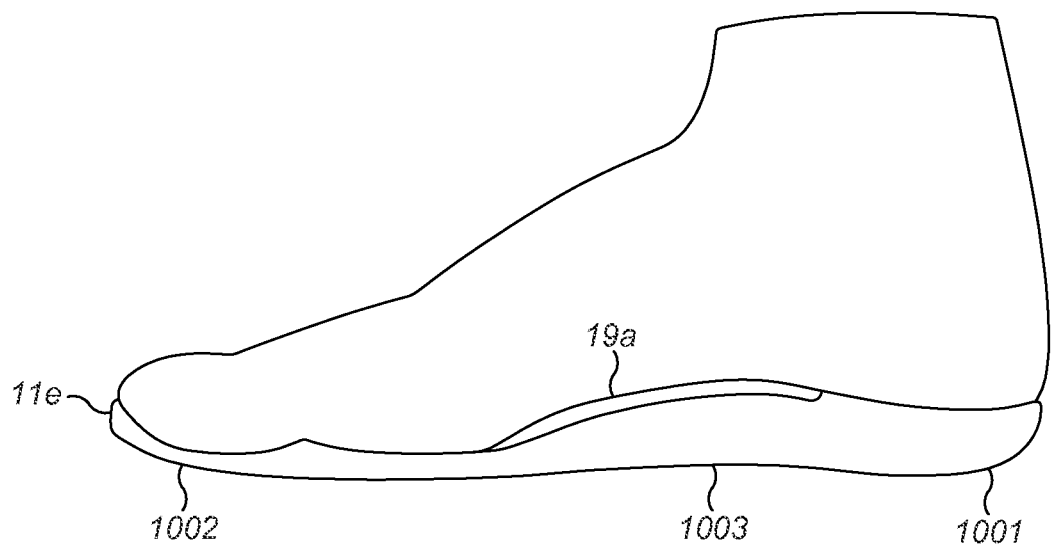
FIG. 10 depicts an exemplary sock.

FIG. 10 shows an exemplary sock 11e. The sock 11e has a heel region 1001 and a toe region 1002, as shown in FIG. 10. The heel region of 1001 may be raised relative to the toe region 1002. This would act to tilt the wearer forward slightly, thus taking pressure off the heel and providing better weight distribution. Between the heel region 1001 and the toe region 1002 of the sock 11e is a raised portion 1003. The bladder 19a is disposed on the raised portion 103. The raised portion 1003 may be designed to match the contours of the plantar plexus or medial plantar arch region of a foot.

As can be seen in FIG. 10, the sock 11e is disposed much more closely to the underside of the foot of a wearer than the bladder shown in FIG. 8. As a result, a smaller bladder 19a can be used as, upon inflating, the bladder 19a needs to cover less distance than the bladder 19 (shown in FIG. 8) as the bladder is disposed much closer to the foot of the wearer. As such, the use of a contoured sock such as the sock 11e shown in FIG. 10 enables a bladder of a smaller volume to be used than is needed for regular flat socks such as the sock 11 shown in FIG. 8.

Alternatively, the same or a similar sized bladder as is used with the flat sock shown in FIG. 8 can be used. When a foot abuts the sock 11e when the boot 101 is being worn, such a bladder 19 would not need to be inflated fully before the pressure limit (for example, 23.4 kPa (3.4 psi)) is reached as it would abut the foot of the wearer before it was fully inflated causing the pressure in the bladder to increase sooner.

Accordingly, when a contoured sock such as the sock 11e is used with the blood flow stimulating means, less energy is required to operate the blood flow stimulating means as less fluid is being transmitted around the system and the bladder 19 or 19a can be inflated in a shorter space of time, both of which result in less fluid being transmitted from the reservoir 29 to the bladder 19 per cycle. Accordingly, the battery life of the blood flow stimulating means is increased.

The bladder 19a may have a volume approximately of 40 cm$^3$.

The bladder may have a volume of up to 40 cm$^3$.

Pressure redistribution is also aided by the sock 11e as it ensures that the plantar aspect of the foot is maximally supported, for example by raised portion 1003 of the sock 11e or a foam, so that the surface area bearing the load is as large as possible, thereby ensuring lowest average pressures across the foot, reducing the likelihood of ulcer formation.

In order to overcome the problem of high heel pressures developing, as described above, a swan line can be incorporated into the boot 101 of the integrated offloading device 110. A swan line is where the heel of a wearer of the boot 101 is held in a position higher than the front of their foot. This would act to tilt the wearer forward slightly, thus taking pressure off the heel and providing better weight distribution.

The swan line can come from the shape of the boot 101 itself or from the shape of the contoured sock 11e.

With regard to the previously described integrated offloading device 10, the flat plate portion 12b, as shown in FIG. 1b, could be shaped such that a swan line is formed. Alternatively, the sock 11, disposed on top of the flat plate portion 12b could be shaped such that a swan line is formed.

Accordingly, any of the integrated offloading devices 10, 110 described herein could configured to include a swan line.

Although the use of contoured socks is known in footwear, the use of contoured socks in integrated offloading devices 110 is not obvious as the foot is offloaded from the sock of the boot and the nature of the contact of the foot with the sock is, therefore, less of a consideration.

Figure 11:
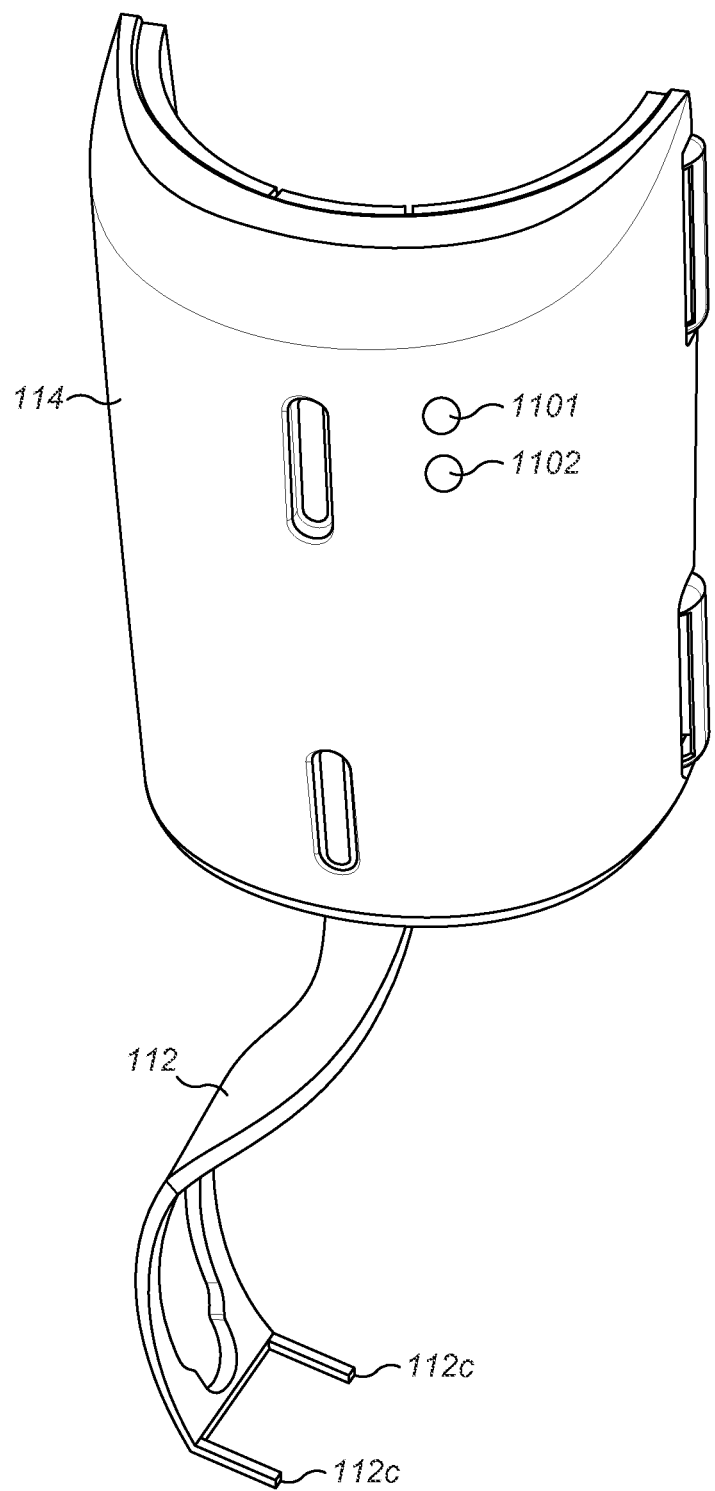
FIG. 11 depicts a shin support structure connected to an offloading element, wherein the shin support structure has a proximity sensor and a pedometer disposed in or on it.

FIG. 11 shows a shin support structure 114 connected to an offloading element 112 wherein the shin support structure has a proximity sensor 1101 and a pedometer 1102 disposed in or on it.

The proximity sensor 1101 is configured to detect when the shin support structure 114 is being worn. A memory (not shown) may be provided to store data produced by the proximity sensor 1101. As such, a record of how often and when the shin support structure 114 is being worn can be kept.

The pedometer 1102 is configured to detect how many steps are taken by a wearer of the shin support structure 114. Likewise, a record of how many steps have been taken can be recorded on the memory.

The data recorded on the memory can be used by a clinician to monitor patient compliance.

FIG. 12 shows an exemplary boot 101 comprising multiple temperature sensors 121a, 121b and 121c. These are disposed abutting the areas of the foot of a wearer that are most prone to skin breakdown.

A battery pack or other energy source (not shown in the Figures) for powering the blood flow stimulating means may be disposed on the outside of the shin support structure 114 such that it can be easily replaced without the wearer of the integrated offloading device 110 having to remove the shin support structure 114.

The proximity sensor 1101 and pedometer 1102 may be mounted in or on the shin support structure 114 and therefore they would be directly wired to or present on an electronics printed circuit board (PCB).

The temperature sensors 121a, 121b and 121c that are in the footwear may be connected to a local electronics PCB installed in the boot 101 and the data from the sensors may be sent to the main PCB in the shin support structure 114 either by wired or wireless connection. The local electronics PCB may be provided within the sock 11, 11a, 11b, 11c, 11d and 11e or within the sole 111 of the boot 101.

Although the present invention has been described in connection with specific exemplary embodiments, it should be understood that various changes, substitutions, and alterations apparent to those skilled in the art can be made to the disclosed embodiments without departing from the scope of the invention as set forth in the appended claims.

The invention claimed is:

1. An offloading support device, comprising:
    a support for, in use, engaging a wearer of the support device;
    a boot comprising an upper and a sole;
    a rigid member disposed within the sole;
    an offloader;
    a first coupling engagement between the offloader and the support, the first coupling engagement comprising a channel in the support that is configured to receive a top end of the offloader, and at least one fastener to securely join the support to the offloader, the first coupling engagement being configured such that, upon insertion of the top end of the offloader into the channel and upon tightening of the at least one fastener, the support is rigidly fixed relative to the offloader to prevent relative movement between the support and the offloader; and
    a second coupling engagement between the offloader and the rigid member, the second coupling engagement comprising a male mating portion on the offloader and a female mating portion on the rigid member, the second coupling engagement being configured such that, upon insertion of the male mating portion of the offloader into the female mating portion of the rigid member, the rigid member is rigidly fixed relative to the offloader to prevent relative movement between the rigid member and the offloader;
    wherein the first coupling engagement between the support and the offloader, and a the second coupling engagement between the offloader and the boot, are both sufficiently rigid so as to immobilize tri-axis ankle movement of a foot of the wearer when a heel of the wearer's foot is engaged with a corresponding heel portion of the sole.

2. The offloading support device of claim 1, wherein the male mating portion comprises at least one extension configured to removably engage the female mating portion of the rigid member via a recess in the sole.

3. The offloading support device of claim 1, further comprising a blood flow stimulating system.

4. The offloading support device of claim 3, wherein the blood flow stimulating system comprises:
    a power supply;
    a fluid pump;
    a fluid reservoir;
    a controller; and
    a bladder.

5. The offloading support device of claim 4, wherein the power supply, the fluid pump, the fluid reservoir and the controller are each disposed either on or in the support and the bladder is disposed within the boot.

6. The offloading support device of claim 1, wherein the offloader is disposed entirely outside of the upper.

7. The offloading support device of claim 1, wherein, in use, the support engages the wearer's leg below a knee.

8. The offloading support device of claim 1, wherein, in use, the offloader passes from a front of a shin of the wearer to a lateral aspect of the boot.

9. The offloading support device of claim 1, further comprising:
    a proximity sensor; and
    a memory for storing data;
    wherein the proximity sensor detects whether the wearer is wearing the support device and data produced by the proximity sensor is stored on the memory.

10. The offloading support device of claim 1, further comprising a blood flow stimulating system, wherein the blood flow stimulating system comprises:
    a power supply;
    a fluid pump;
    a fluid reserve;
    a controller;
    a bladder; and
    a proximity sensor, wherein the proximity sensor detects whether the offloading support device is being worn and the controller is configured to disable the bladder when the proximity sensor does not detect that the support device is being worn.

11. The offloading support device of claim 1, further comprising a temperature sensor disposed within the boot, in or on the sole and/or the upper, configured to indicate a rise in temperature being indicative of skin breakdown on the foot of the wearer of the support device.

12. The offloading support device of claim 1, wherein the first and second coupling engagements are configured to prevent pressure hot spots on a sole of the foot of the wearer.

* * * * *